(12) United States Patent
Gutermuth et al.

(10) Patent No.: US 11,919,206 B2
(45) Date of Patent: Mar. 5, 2024

(54) METHOD FOR PRODUCING A NEURONALLY INDUCTIVE CULTIVATION MATRIX

(71) Applicant: FRAUNHOFER-GESELLSCHAFT ZUR FÖRDERUNG DER ANGEWANDTEN FORSCHUNG E.V., Munich (DE)

(72) Inventors: Angela Gutermuth, Aachen (DE); Christoph Baum, Cologne (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 455 days.

(21) Appl. No.: 16/608,460

(22) PCT Filed: Mar. 15, 2018

(86) PCT No.: PCT/EP2018/056590
§ 371 (c)(1),
(2) Date: Oct. 25, 2019

(87) PCT Pub. No.: WO2018/206185
PCT Pub. Date: Nov. 15, 2018

(65) Prior Publication Data
US 2021/0115393 A1    Apr. 22, 2021

(30) Foreign Application Priority Data

May 8, 2017    (DE) .................... 10 2017 207 698.4

(51) Int. Cl.
*B29C 37/00*    (2006.01)
*C12N 5/00*    (2006.01)
(Continued)

(52) U.S. Cl.
CPC ........ *B29C 37/0053* (2013.01); *C12N 5/0068* (2013.01); *C12N 5/0618* (2013.01);
(Continued)

(58) Field of Classification Search
CPC .................. B29C 2059/023; G03F 7/0002
See application file for complete search history.

(56) References Cited

U.S. PATENT DOCUMENTS 9,427,908 B2 * 8/2016 Low ................ B29C 59/022
10,899,044 B2 * 1/2021 Heilmann ............ C25D 11/24
(Continued)

FOREIGN PATENT DOCUMENTS

CN        104774808 A      7/2015
DE    102015205534 A1      9/2016
(Continued)

OTHER PUBLICATIONS

Tang, Min D., Andrew P. Golden, and Joe Tien. "Molding of three-dimensional microstructures of gels." Journal of the American Chemical Society 125.43 (Oct. 4, 2003): 12988-12989. (Year: 2003).*

(Continued)

*Primary Examiner* — Benjamin A Schiffman
(74) *Attorney, Agent, or Firm* — Harness, Dickey & Pierce, P.L.C.; Stephen T. Olson

(57) ABSTRACT

A matrix for the cultivation of biological cells and differentiation into neuronal cells consists of a polymer base body having a structured surface with a microstructure and a nanostructure embedded therein.

6 Claims, 2 Drawing Sheets

(51) Int. Cl.
*C12N 5/079* (2010.01)
*B29C 39/00* (2006.01)
*B29C 39/02* (2006.01)
*B29C 59/00* (2006.01)
*B29C 59/02* (2006.01)
*C12M 1/12* (2006.01)

(52) U.S. Cl.
CPC .......... *B29C 39/003* (2013.01); *B29C 39/026* (2013.01); *B29C 59/005* (2013.01); *B29C 59/022* (2013.01); *B29K 2005/00* (2013.01); *B29K 2089/00* (2013.01); *C12M 25/14* (2013.01); *C12N 2533/54* (2013.01); *C12N 2535/00* (2013.01); *C12N 2537/00* (2013.01)

(56) References Cited

U.S. PATENT DOCUMENTS

| | | | | |
|---|---|---|---|---|
| 2013/0211542 | A1* | 8/2013 | McKee | B29C 35/0805 264/494 |
| 2015/0284669 | A1* | 10/2015 | Choudhury | C12M 25/06 435/402 |
| 2017/0204366 | A1 | 7/2017 | Sasaki et al. | |
| 2018/0104046 | A1 | 4/2018 | Gutermuth | |
| 2020/0348588 | A1* | 11/2020 | Kirner | B29C 59/022 |
| 2021/0115393 | A1 | 4/2021 | Gutermuth et al. | |

FOREIGN PATENT DOCUMENTS

| | | |
|---|---|---|
| JP | 2014138605 A | 7/2014 |
| JP | 2017055761 A | 3/2017 |
| WO | 2013126329 A1 | 8/2013 |

OTHER PUBLICATIONS

Gläbe, Ralf, and Oltmann Riemer. "Diamond machining of micro-optical components and structures." Micro-Optics 2010. vol. 7716. SPIE, May 6, 2010. (Year: 2010).*

Evans, Chris J., and James B. Bryan. ""Structured", "textured" or "engineered" surfaces." Cirp Annals 48.2 (1999): 541-556. (Year: 1999).*

Vecchione, Raffaele, et al. "Confined gelatin dehydration as a viable route to go beyond micromilling resolution and miniaturize biological assays." ACS applied materials & interfaces 8.19 (May 3, 2016): 12075-12081. (Year: 2016).*

Heamawatanachai, Sumet, and Eberhard Bamberg. "Design and characterization of a PZT driven micromachining tool based on single-point tool tip geometry." Precision engineering 33.4 (Nov. 12, 2008): 387-394. (Year: 2009).*

Kim, Se-jeong, et al. "Hydrogels with an embossed surface: an all-in-one platform for mass production and culture of human adipose-derived stem cell spheroids." Biomaterials 188 (Oct. 22, 2018): 198-212. (Year: 2019).*

Selimović, Šeila, et al. "Microscale strategies for generating cell-encapsulating hydrogels." Polymers 4.3 (Sep. 5, 2012): 1554-1579. (Year: 2012).*

Xia et al. Soft Lithography, Annual Review of Materials Science, vol. 28, pp. 153-184, Aug. 1998 (Year: 1998).*

Song, Liyuan, et al. "Surface-patterning of nanocomposite hydrogel film by direct replica molding and subsequent change in pattern size." Polymer journal 40.9 (Jul. 9, 2008): 800-805. (Year: 2008).*

Kang, Gyumin, et al. "Agarose microwell based neuronal micro-circuit arrays on microelectrode arrays for high throughput drug testing." Lab on a Chip 9.22 (Sep. 10, 2009): 3236-3242. (Year: 2009).*

Joo, Sunghoon, Jisoon Lim, and Yoonkey Nam. "Design and fabrication of miniaturized neuronal circuits on microelectrode arrays using agarose hydrogel micro-molding technique." BioChip Journal 12 (Jul. 10, 2018): 193-201. (Year: 2018).*

Claudia Skazik-Voogt et al: "Fertigungsverfahren fur das Tissue Engineering", GIT-Labor—Portal fur Anwender in Wissenschaft und Industrie, Retrieved from the Internet: URL: https://www.git-labor.de/forschung/life-sciences-biotechnologie/fertigungsverfahren-fuer-das-tissue-engineering [retrieved on May 2, 2018] the whole document, abstract paragraph [vorletzter]—last paragraph.

Angela Gutermuth: "Masterarbeit Life Sciences Engineering", Nov. 1, 2015 (Nov. 1, 2015), XP055471842, Retrieved from the Internet: URL :<https://fsbio.rwth-aachen.de/sites/def> ault/files/fsfiles/Ausschreibung%20Mastera rbeit_Fraunhofer%20IPT.pdf [retrieved on May 2, 2018] the whole document.

Bilder zu (Pictures of) "Fertigungsverfahren für das Tissue Engineering" vom Dec. 4, 2017.

International Search Report (in English and German) and Written Opinion (in German) issued in PCT/EP2018/056590, dated May 28, 2018; ISA/EP.

International Search Report for PCT/EP2018/056590, Fraunhofer-Gesellschaft Zur Förderung Der Angewandten Forschung E.V., dated Nov. 21, 2019, with English translation.

Chinese Office Action received in corresponding matter CN 2018800283011, dated Feb. 2, 2023.

Second Chinese Office Action regarding Application No. 201880028301.1 dated Sep. 28, 2023.

* cited by examiner

METHOD FOR PRODUCING A NEURONALLY INDUCTIVE CULTIVATION MATRIX

CROSS-REFERENCE TO RELATED APPLICATIONS

This application is a 371 U.S. National Phase of International Application No. PCT/EP2018/056590, filed Mar. 15, 2018, which claims the benefit of German Patent Application No. 10 2017 207 698.4, filed May 8, 2017. The entire disclosures of the above applications are incorporated herein by reference.

FIELD

The invention relates to methods and means for producing neuronal cells and tissues from isolated cells, especially stem cells, outside the human or animal body.

BACKGROUND

There is a need in research and therapy for neuronal cells and neuronal tissue from human and autologous cell material for the purposes of cell therapy and patient-specific drug development. There is also a desire for genotypically identifiable and definable neuronal cell lines for research purposes.

Methods for producing neuronal cells or tissues from stem cells or other pluripotent or plastic cells are known. These methods are based on xenobiotic differentiation factors. However, the use of such factors leads to adverse changes in the cells to be differentiated and also makes their approval, for example as a medical device or therapeutic agent, more difficult. Other known methods for producing autologous neuronal cells are based on reprogramming adult tissue cells to a pluripotent status, which is then differentiated into the desired neuronal cell. For example, so-called IPS cells can be reprogrammed from somatic fibroblasts. However, known reprogramming methods are based on virus transformation. Therefore, the pluripotent cells produced in this manner are not readily usable without side effects and are not approved as a medical device or therapeutic agent. In addition, the efficiency of reprogramming adult fibroblasts into neuronal cells is very low and is less than 0.2% according to research. The differentiation of these pluripotent cells into neuronal cells is achieved using chemical neuronal differentiation factors and/or by viral transfection. The neuronal cells generated by means of viral transfection can only be used for drug testing because they can be carcinogenic.

One method that can largely or completely dispense with chemical differentiation factors or even viral factors is mechanotransduction. In this case, stem cells or other pluripotent or plastic cells are stimulated by specific mechanical stimulation to form a cell-typical topography and ultimately a cell-typical function. There have been initial approaches to mechanotransductive neural differentiation of stem cells. These approaches are based on photolithographically generated structures that are, for example, molded on silicone elastomer (polydimethylsiloxane, PDMS), for example. On the one hand, such methods only allow the production of very small areas, so that only small amounts of neuronal cells can be differentiated. In addition, differentiation efficiency has not proved sufficient in this case, and the quality of function and structure of the cells actually differentiated as neurons is in need of improvement.

SUMMARY OF THE INVENTION

The present invention was based on the technical problem of providing methods and means for producing neuronal cells or tissues from isolated biological cells, in particular stem cells, which methods and means enable uncomplicated and economically attractive production of, in particular, autologous neuronal cells or tissues in large quantities and high quality. Therefore, it was necessary to improve both known methods of mechanotransductive differentiation with regard to the efficiency and quality of differentiation into neuronal cells, as well as to develop methods that allow the production of a large number of neuronal cells or tissues.

The invention solves the underlying technical problem firstly by providing a cultivation matrix (cultivation substrate) for cultivating biological cells that have been seeded on it, in particular pluripotent or plastic cells, and for differentiating these cells into neuronal cells or neuronal tissue. According to the invention, the matrix comprises at least, or preferably exclusively, one base body made of biocompatible polymer or polymer of biological origin (biological polymer) that has a surface structured according to the invention. This special surface structure is characterized by a periodic microstructure made of parallel microdimensioned grooves or channels, or alternatively ridges, and a periodic nanostructure made of parallel nanodimensioned grooves or channels, or alternatively ridges, wherein, according to the invention the periodic nanostructure runs parallel to the periodic microstructure, and the periodic nanostructure is embedded into the microstructure at regular intervals, that is, into the period of the microstructure, that is, in the grooves or channels, or alternatively on the ridges, of the microstructure. This means in particular that a periodic microstructure and a periodic nanostructure alternate on the structured surface. A regular pattern made of mutually parallel grooves, channels, or ridges is preferred according to the invention.

BRIEF DESCRIPTION OF THE DRAWINGS

The invention is described in greater detail below:

FIG. 3A illustrates a cultivation matrix having the structure according to the schematic representation (not to scale) according to FIG. 1.

DETAILED DESCRIPTION

Figure 1:
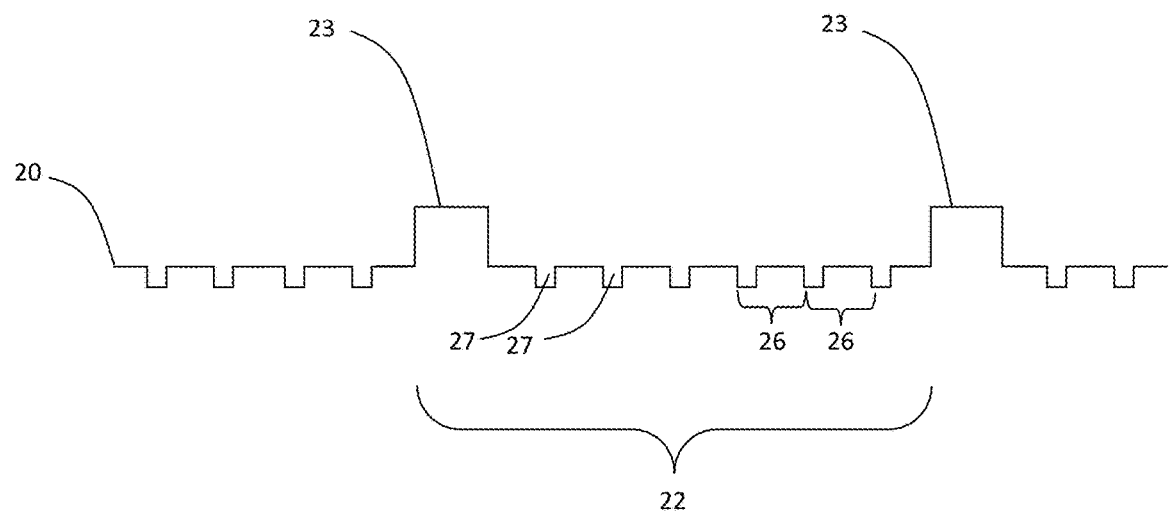
FIG. 1 is a detailed view of a schematic cross section through a neurotransductive cultivation matrix of the invention. The latter comprises a base body having a structured surface (20). The surface (20) is characterized by a microstructure (22) of parallel microdimensioned ridges (23) and a periodic nanostructure (26) embedded therebetween having parallel nanodimensioned grooves (27) running parallel to the microstructure (22).
Figure 2:
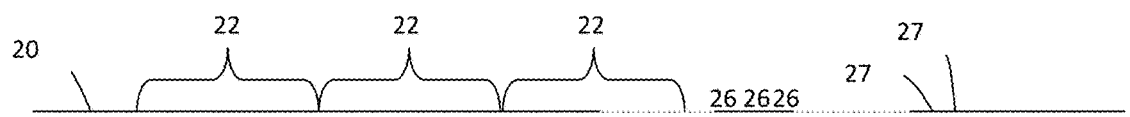
FIG. 2 is a different magnification of a schematic cross section through another variant of a neurotransductive cultivation matrix of the invention. A structured surface (20) is embodied on one side on the base body (10) of the matrix. The structured surface is characterized by a periodic microstructure (22) having parallel microdimensioned grooves (23) and a periodic nanostructure (26) having parallel nanodimensioned grooves (27) running parallel to the microstructure (22), the periodic nanostructure (26) being embedded in the grooves (23) of the microstructure (22).

Surprisingly, it has been found that, in the course of cultivation, the biological cells seeded on this specific structured surface orient themselves in their growth along both the parallel microdimensioned and nanodimensioned grooves or ridges such that, due to the mechanotransduction thus triggered, neuronal cells develop from the seeded individual cells and, ultimately, neuronal tissue with a clearly neuronal structure and neural function develops in a stable and reliable manner. The differentiation efficiency on the inventively structured surface of the cultivation matrix is extraordinarily high.

These positive effects can be increased even further. In one preferred embodiment, the biocompatible or biological polymer of the base body, at least in the region of the structured surface, has a rigidity (mechanical strength) that equals the corresponding mechanical property (rigidity) of the biological cells, is preferably not greater than this rigidity, and is particularly preferably less than this rigidity. Contrary to previous ideas, it has been shown that a structured surface that is comparatively flexible and less rigid significantly improves the efficiency of the mechanotransduction and the quality of the neuronal cells and tissue produced. The rigidity of the structured surface of the matrix is preferably determined by the selection of the biocompatible or biological polymer and/or its composition or manner of production. As is known, the mechanical properties of such polymers can be adjusted by selecting the composition and/or by the manner of crosslinking. Suitable polymer materials are described below. A gel-like polymer matrix is preferred.

Surprisingly, the inventors found that particularly high differentiation efficiency and quality of the obtained differentiated neuronal cells and tissue can be achieved using a very specific dimensioning of the parallel grooves or channels, or alternatively ridges, of the inventively microstructured and nanostructured surface of the matrix. Surprisingly, it was in this case found that the in particular highly periodic alternation of a low periodic microstructure with a higher periodic nanostructure enables particular success in differentiation. That is, multiple periods of the nanostructure are embedded in one period of the microstructure. The microstructure made of grooves or channels, or alternatively of ridges, is preferably formed with a depth, or height, of 0.7 to 1.5 µm and a width of 1 to 2 µm. The individual grooves or channels, or alternatively ridges, of the microstructure have a center distance (period) of 3 to 12 µm from one another. It has been demonstrated that the dimensioning of the structures is of great importance in this context. In one particular embodiment, the grooves of the microstructure are embodied as channels. In one alternative embodiment, correspondingly dimensioned ridges are embodied instead of the grooves of the microstructure (negative mold).

The nanostructure, which is embedded in the abovementioned microstructure, is preferably formed from grooves or channels, or alternatively ridges, having a depth, or height, of 15 to 35 µm and a width of 450 to 550 µm. The individual grooves or channels, or alternatively ridges, of the nanostructure have a center distance (period, i.e. pitch) of 500 to 550 µm from one another. It has been demonstrated that the dimensioning of the structures is of great importance in this context. In one particular embodiment, the grooves of the nanostructure are embodied as channels. In one alternative embodiment, correspondingly dimensioned ridges are embodied instead of the grooves of the nanostructure (negative mold).

In one particular variant, the microstructure is formed as grooves or channels, and the nanostructure embeddedd in the groove or channel of the microstructure is embodied as grooves or channels. In one alternative variant, the microstructure is embodied as grooves or channels, and the nanostructure embedded in the groove or channel of the microstructure is embodied as ridges. In one alternative variant, the microstructure is embodied as ridges and the nanostructure embedded on the ridge of the microstructure is embodied as grooves or channels. In one alternative variant, the microstructure is embodied as ridges, and the nanostructure embedded on the ridge of the microstructure is embodied as ridges.

In a second aspect, the invention provides a novel method for producing such a neuronally inductive cultivation matrix, wherein the structured surface is produced on the base body of the matrix using microstructuring methods, but especially using machining methods, of the biocompatible or biological polymer of the base body. According to the invention, it is preferred that the periodic microstructure and the periodic nanostructure embedded therein are formed, specifically together in a single microstructuring work step.

The inventive microstructuring method is a machining method using a machining tool moved relative to the material being machined and is preferably selected from: planing, bumping, and milling. The machining method is preferably a method using a stationary machining tool with a moving material to be machined, specifically turning in particular. The microstructuring method is particularly preferably turning with a turning tool.

In one preferred embodiment, this machining operation is carried out with a cutting tool, that is, specifically a blade, turning tool, or milling cutter, that has a cutting edge with a tip radius ($r_E$) of less than 10 µm and is preferably constructed from monocrystalline diamond. Surprisingly, it been found that the specific structuring described herein can be obtained in a particularly simple and reliable manner by using such a cutting tool with such a cutting edge. The nanostructure together with the microstructure may preferably be produced in a single processing step. The nanostructure is directly dependent on the advance of the cutting tool (per revolution or per stroke) and the tip radius ($r_E$).

The tip radius ($r_E$) of the machining tool cutting edge is preferably 5 µm or less than 5 µm, 2 µm or preferably less than 2 µm, or 1 µm or preferably less than 1 µm, or 500 nm or less than 500 nm. The machining tool is pointed in one variant; in another variant, the machining tool is faceted. A trailing cutting edge is preferably avoided. An MDC cutting tool with a 1×30° tip angle and tool radius ($r_E$) of 2 µm or 1 µm is preferred. An advance of 500 to 550 nm, corresponding to the period (pitch) of the nanostructuring to be produced.

In one preferred variant, this machined microstructuring is applied directly to the polymeric base body of the matrix by means of this method in order to obtain directly the inventively structured neuronally inductive surface. In one alternative and preferred variant, this surface structure is first embodied on a tool in this manner, preferably as a negative mold, and then subsequently the actual neuronally inductive surface is produced on the base body of the matrix from biocompatible or biological polymer by means of this surface-structured tool. It is preferred that the polymer of the base body, preferably still in liquid form, is cast onto the surface-structured tool, that is, at least onto the structured surface embodied on the tool after the microstructuring. In one alternative and preferred variant, the polymer of the base body is embossed with this tool so that the structured surface is embodied on the base body. It is optionally provided in each case that the polymer itself cures or dries on the structured surface of this tool and then the thus surface-structured matrix, in cured and/or dried form, is separated from the tool, that is, in particular, is lifted off of it. In one preferred embodiment, in a further step for using the matrix, the cured or, in particular, the dried polymeric base body is brought into contact with liquid, in particular culture medium, thereby producing its desired final shape and mechanical stiffness by swelling and hydration. The base body is preferably finished and stored in dry form, and the swelling and hydration are not conducted until use for cultivating cells. The surface-structured tool can be used repeatedly to produce additional neuronally inductive cultivation matrices of the invention. The cultivation matrices can be easily produced in large numbers by means of this embossing or casting method. In addition, the simple structuring method allows the provision of larger surface-area neuronally inductive cultivation matrices so that large-area neuronal cell populations and neuronal tissue can also be produced.

In one special embodiment, the surface-structured tool is thus designed as an embossing die or as an embossing roller. The embossing of the inventively structured surface onto liquid or just-cured polymer gel is similar to that used in printing technology. Large quantities and large areas of cultivation matrix for the production of neuronal cells or tissue can also be thus produced.

The biocompatible polymer should be hydrophilic enough to allow cell adhesion. The biocompatible or biological polymer is preferably selected from the group of biomaterials comprising collagen, agarose, and derivatives thereof, and semi-synthetic modifications thereof, such as meta-acrylated gelatin (GelMA). Polymers that are initially present in liquid form before they assume a gelatinous state are preferred. Particularly preferred is lyophilized collagen. Alternatively preferred is meta-acrylated gelatin (GelMA).

Particularly preferred is a method for producing matrices having neurotransductive topography, wherein a liquid polymer, especially a solution lyophilized collagen, is cast onto a tool having an inventively structured surface, is cured there, and is dried. The drying time depends on the volume, surface, and type of gel. Drying is preferably carried out by means of a desiccator. The molded inventive neuroinductive topography is easily retained for a few weeks in the matrix substrates that can be used. In this way, matrices can be produced simply and in large numbers for the formation of neuronal cells or tissues and stored for use. When the cells are seeded in suspension, the dried gel matrix swells and then exhibits its originally imprinted neuroinductive surface structuring.

In particular, elastic materials such as silicone elastomers (RTV) or polyurethanes are suitable as casting or embossing tools. Alternatively, poorly elastic or inelastic flexible films or rigid materials may be used. Metals are preferably provided as the material for the casting or embossing tool. These are preferably selected from non-ferrous metals, especially copper, copper-containing alloys, or nickel-containing alloys. Plastics are alternatively preferred as the material for the casting or embossing tool.

Particularly preferred is an embossing tool that is a metal or plastic cylinder that is rotated by means of rotation with the cutting tool described herein and thus provided with microstructure and nanostructure. In this preferred embodiment, the molding process for producing the surface structuring matrix is a film embossing process.

In another aspect of the invention, the neuronally inductive matrix described herein is used for mechanotransductive differentiation of stem cells into neuronal tissue.

Finally, in a further aspect, the invention provides a novel method for producing neuronal cells or tissues from isolated biological cells, specifically from stem cells, pluripotent cells, or plastic cells. This method includes at least the steps of contacting isolated biological cells with the neuronally inductive matrix of the present invention, then cultivating the biological cells on or at the structured surface of this matrix, wherein mechanotransductive differentiation of these cells to neuronal cells and/or neuronal tissue occurs, wherein differentiated neuronal cells and/or neuronal tissue is obtained.

It is preferably provided that the neuronal cells or tissue embedded in this matrix may be reused. In one alternative embodiment, the neuronal cells or the neuronal tissue is detached from the matrix in a manner known per se. Optionally, the neuronal cells are detached from the matrix and then separated into a suspension. The suspension of neuronal cells can be further cultivated.

The cultivation matrix according to the invention advantageously also allows differentiation of less plastic cells even from adult tissue. Cells from adipose tissue, bone marrow, or skin are preferred. Cells obtained from umbilical cord blood are also preferred. The isolated biological cells that are to differentiate into neuronal cells are preferably stem cells, preferably mesenchymal stem cells (MSC); in this way differentiated MSC, especially autologous MSC, are obtained. For example, mesenchymal stem cells can be taken from the adipose tissue of an autologous donor and isolated. The use of such cells for therapy is approved and ethically fully acceptable. A patient is immediately treated with his own cells from his adipose tissue.

These obtained neuronal cells or tissues can be used immediately in patient therapy and prophylaxis as patient-specific cells in particular, i.e. as a medical device.

The obtained neuronal cells or tissues can also be used as in particular patient-specific cells, also for drug development, in particular also for the development of patient-specific medications, and for patient treatment and prophylaxis.

EXAMPLE

The entire process sequence for the mechanotransductive differentiation of stem cells into neuronal cells or neuronal tissue includes (a) production of a master tool having the negative of the inventive topography, (b) transfer of the topography onto a moldable material, (c) optionally further impressions from the master tool; and (d) cultivating stem cells on the molded, structured material.

To produce a surface-structured master tool, a cylindrical roller made of copper or nickel (or corresponding alloys) is clamped in a lathe and turned with an MDC cutting edge having a tip angle of 1×30° and a tip radius of 1 µm at a speed of 150 min$^{-1}$ by means of a turning tool. The machining tool is guided such that ridges having a width of 1.2 µm and spacing of 11.2 µm are cut on the cylinder (topography 1). Alternatively, the advance is set such that ridges having a width of 1.24 µm and spacing of 3.8 µm are produced on the cylinder (topography 2). The ridges form the microstructure.

For machining, an advance of 0.5 mm per revolution (or tool stroke) is selected. Between the ridges of the microstructure, a nanostructure having channels of 32 nm, which are spaced 500 nm apart from one another (topography 1), or channels having a depth of 19.15 nm and set 40 nm apart from one another, is formed on the metal cylinder (topography 2).

The surface-structured master tool produced in this way is clamped as an embossing roller in an apparatus for embossing collagen films. A base body made of freshly poured lyophilized collagen is used as collagen film. The channel structure of the roller is embossed into the surface of the collagen film. Then the collagen film having a structured surface is dried by dehydration in a desiccator.

In an alternative approach, a correspondingly structured flat metal plate is produced by planing with a corresponding machining tool. The metal plate acts as a template. A freshly prepared liquid solution of lyophilized collagen is cast onto it and allowed to harden there. Then the collagen film produced is dried in the desiccator for about four days. The film shrinks by a few percent. It may be removed easily from the template due to shrinkage.

In a further alternative approach, a correspondingly structured flat casting mold made of silicone elastomer is produced by foil embossing or casting by means of a metal master tool. This mold is then used as a template accordingly.

The liquid solution of lyophilized collagen is cast onto the mold and allowed to harden there. Then the collagen film produced is dried in the desiccator for about four days. The film shrinks by a few percent. It may be removed easily from the template due to shrinkage. Alternatively, due to its elasticity, the casting mold is removed from the solidified or dried collagen gel.

It has been found that the embossed or cast collagen film can be stored for several weeks after drying. In the present case, the embossed film was moistened after a storage period of four weeks, so that the original shape, including the inventively structured surface, formed.

Figure 3A:
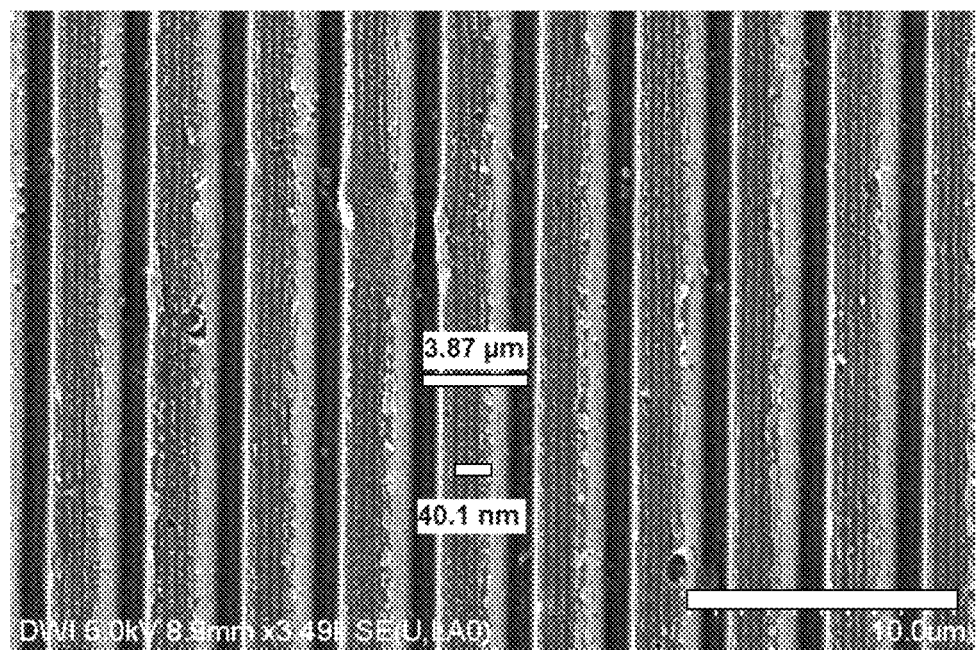
FIGS. 3A and 3B show a plan view of electron micrographs of inventively surface-structured cultivation matrices (scales added).
Figure 3B:
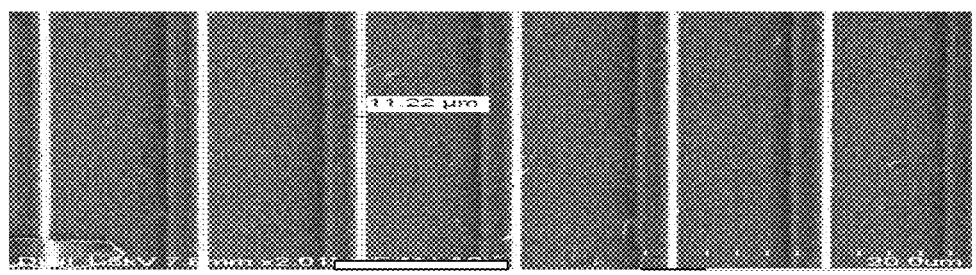

The freshly embossed or rehydrated collagen foil is used as a cultivation matrix. The surface structure of the cultivation matrix is shown in FIG. 3. FIGS. 3A and 3B illustrate SEM images of a surface-structured gelatin matrix (metacrylated gelatin) that was embossed with a tool having topography 1. The surface-structured gelatin matrix was produced in a comparable manner, as described here by way of example for a collagen matrix. FIG. 3A illustrates a gelatin matrix molded with a nickel master tool. FIG. 3B illustrates a gelatin matrix molded with a PDMS master tool.

Both the cast or embossed collagen film and the embossed gelatin matrix can be readily stored in the dried state for at least 3 weeks, so that the originally embossed surface structuring is retained after water or culture medium is added when swelling the gels.

For producing neuronal cells, suspended mesenchymal stem cells derived from adult tissue are seeded onto the embossed gelatin matrix or collagen film and cultivated for four weeks.

The cultivated cells develop an extension and parallel alignment of their morphology along the microstructuring of the surface of the cultivation matrix. The cells lose their original fibroblast-like shape rapidly, and the typical morphology of neuronal cells is recognizable after a few days. The cells develop very long dendritic or axonal extensions, this determining their good function as nerve cells.

The residual collagen of the collagen matrix is digested using collagenase after a four-week cultivation period so that the cells can be gently isolated without destroying their acquired morphology. Vitality tests demonstrate that there is no limitation to the vitality of these cells following collagenase digestion. In assays, neuronal markers were detected in the cells at the gene and protein levels.

The invention claimed is:

1. A method for producing a matrix for cultivating biological cells and differentiating the biological cells into neuronal cells or neuronal tissue, the matrix comprising a base body made of biocompatible or biological polymer having a structured surface, a first periodic microstructure made of parallel microdimensioned grooves, and a second periodic nanostructure, the second periodic nanostructure made of parallel nanodimensioned grooves, and the second periodic nanostructure extending parallel to the first periodic microstructure and embedded into the parallel microdimensioned grooves of the first periodic microstructure, the method comprising:
    forming a structured surface on a tool by machining, wherein the machining is performed with a machining tool having a cutting edge made of monocrystalline diamond with a tip radius of 10 µm or less and the first periodic microstructure and the second periodic nanostructure embedded therein are formed as a negative mold, and
    producing the structured surface on the base body made of biocompatible or biological polymer by:
        casting the polymer of the base body onto the tool, or, embossing of the polymer of the base body with the tool, and
        drying the polymer of the base body on the tool and separating the dry base body from the tool,
        wherein the matrix is obtained as the base body having a structured surface.

2. The method according to claim 1, wherein the polymer is selected from collagen, gelatin, agarose, derivatives and semi-synthetic modifications thereof.

3. The method according to claim 1, wherein the polymer has a rigidity on the structured surface equal to or not greater than the rigidity of the biological cells to be cultivated there.

4. The method according to claim 1, wherein the first periodic microstructure is formed from grooves having a depth of 0.7 to 1.5 µm and a width of 1 to 2 µm that have a center distance of 3 to 12 µm from one another.

5. The method according to claim 1, wherein the second periodic nanostructure is formed from grooves having a depth of 15 to 35 nm and a width of 450 to 550 nm that have a center distance of 500 to 550 nm to each other.

6. The method according to claim 1, wherein the structured surface on the base body is produced by embossing the polymer of the base body with the tool formed as an embossing roller.

* * * * *